United States Patent [19]
Farnum et al.

[11] 3,940,617
[45] Feb. 24, 1976

[54] METHOD FOR NONDESTRUCTIVE FUEL ASSAY OF LASER FUSION TARGETS

[75] Inventors: Eugene H. Farnum; R. Jay Fries, both of Los Alamos, N. Mex.

[73] Assignee: The United States of America as represented by the United States Energy Research and Development Administration, Washington, D.C.

[22] Filed: Apr. 7, 1975

[21] Appl. No.: 565,932

[52] U.S. Cl. ............... 250/303; 250/336; 250/496; 250/502
[51] Int. Cl.² ......................................... G01T 1/61
[58] Field of Search ......... 250/303, 336, 364, 393, 250/432, 496, 526, 502, 501

[56] References Cited
UNITED STATES PATENTS

| | | | |
|---|---|---|---|
| 3,387,136 | 6/1968 | Acree et al. | 250/496 |
| 3,453,196 | 7/1969 | Sporek | 250/526 |
| 3,833,815 | 9/1974 | Fowler | 250/496 |

*Primary Examiner*—Harold A. Dixon
*Attorney, Agent, or Firm*—Dean E. Carlson; Edward C. Walterscheid

[57] ABSTRACT

A method for nondestructively determining the deuterium and tritium content of laser fusion targets by counting the x rays produced by the interaction of tritium beta particles with the walls of the microballoons used to contain the deuterium and tritium gas mixture under high pressure. The x rays provide a direct measure of the tritium content and a means for calculating the deuterium content using the initial known D-T ratio and the known deuterium and tritium diffusion rates.

4 Claims, 7 Drawing Figures

METHOD FOR NONDESTRUCTIVE FUEL ASSAY OF LASER FUSION TARGETS

BACKGROUND OF THE INVENTION

This invention relates to laser fusion targets and more particularly to a nondestructive method for determining the deuterium and tritium content of such targets.

Hollow, spherical, DT-gas-filled targets with diameters ranging from 30 to greater than 200 $\mu$m and with contained fuel pressures varying from 10 to 1000 atm (at 298 K) are of interest for laser fusion. Presently, the primary gas-containment vessels of these targets are either glass microballoons or compositemetal microballoons made by electroless nickel plating of commercially available nickel/manganese/silicon alloy microballoon mandrels. These mandrels are sold under the tradename Solacells by the Solar Division of International Harvester Co., San Diego, CA.

The targets are filled by diffusing DT fuel gas through the walls at elevated temperatures, taking advantage of the exponential temperature dependence of the permeability to allow the gas to be retained for useful times at room temperature. Thus, when the microballoons are placed in a deuterium andd tritium gas mixture of a desired ratio at high pressure and elevated temperature, the deuterium and tritium readily enter the microballoons and equilibrate to the surrounding gas pressure. When the microballoons are cooled to room temperature, the diffusion rate through their walls is greatly reduced, so that the DT mixture within the microballoons remains at high pressure for times which permit useful storage before the targets are irradiated by the laser. However, because the probability of occurrence of submicroscopic pores and other defects in the walls of the microballoons is rather high, the permeation rates of the DT through the walls can vary substantially at room temperature. Accordingly, it is highly desirable to have some means for nondestructively verifying that any particular microballoon laser target does indeed contain the desired amount of DT fuel gas.

SUMMARY OF THE INVENTION

The deuterium and tritium contents of laser fusion target microballoons are nondestructively determined by (a) counting the x-rays produced by the interaction of tritium beta particles with the walls of the microballoons, (b) comparing the number of counts for a designated period of time with a calibration curve of counts for various tritium contents for the same designated time period to obtain the tritium content, and (c) calculating the deuterium content utilizing the known initial D-T ratio and the known diffusion rates for deuterium and tritium.

The method may be used to assay the tritium content—and hence the deuterium content also—of any type of microballoon of a material and having a wall thickness which permit a measurable amount of x-rays to be transmitted from the microballoon. It is particularly well suited to assay of the fuel content of glass or metal microballoons having wall thicknesses in the range of 0.5 to 20 $\mu$m.

DESCRIPTION OF THE PREFERRED EMBODIMENT

Basis for the Method

Figure 1:
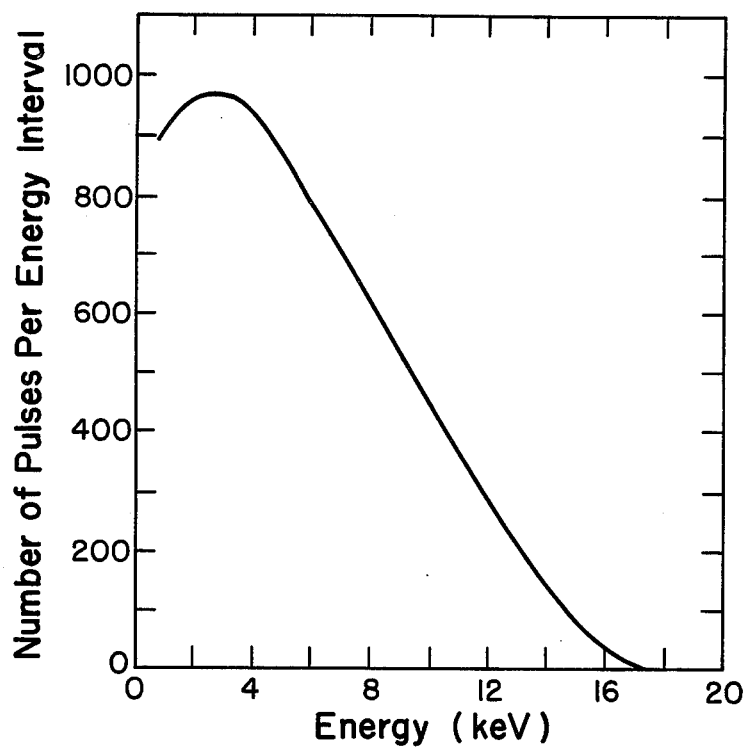
FIG. 1 shows the tritium beta particle energy spectrum.

The method of this invention is predicated on the fact that the walls of the microballoons, which are typically in the range of 0.5 to 20 $\mu$m, are sufficiently thick that there is a substantial interaction of tritium beta particles therein to produce x-ray photons but sufficiently thin that a substantial amount of the x rays thus produced are transmitted through the walls. The tritium beta spectrum, as shown in FIG. 1, has a maximum at about 3 keV and a high-energy cutoff at about 18 keV. The mean beta particle energy is about 5.7 keV. The range of an 18-keV electron in the Solacell microballoons is about 0.8 $\mu$m, which is less than the wall thickness. Accordingly, all beta particles are captured in the Solacell walls. The range of beta particles is somewhat longer in glass (1 $\mu$m at 10 keV; 2 $\mu$m at 14 keV; and 3.3 $\mu$m at 18 keV) so that the highest-energy beta particles can escape from the glass microballoons which typically have wall thicknesses ranging from 1 to 2.5 $\mu$m.

Figure 2:
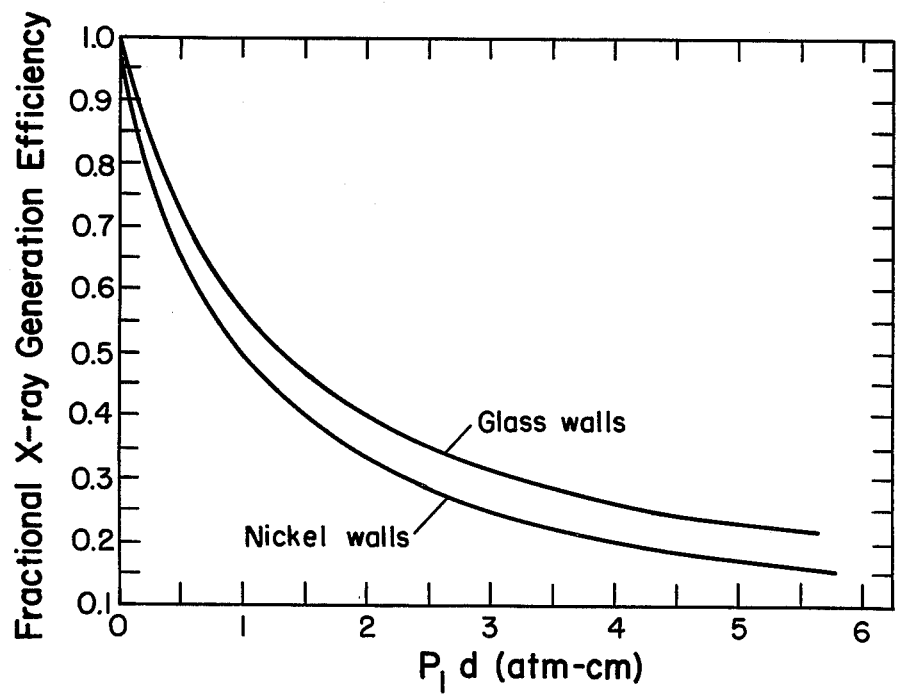
FIG. 2 shows tritium beta particle self-absorption corrections for glass and nickel microballoons.

Absorption of the tritium beta particles in the high-pressure gas within the microballoons (self absorption) is nonnegligible and is also pressure dependent. The combined effects of this self absorption, beta particle backscatter by the microballoon walls, and x-ray generation in the gas must be taken into account in determining the relationship of x-rays counted to the amount of tritium present. In FIG. 2, the relative efficiency of x-ray photon generation is plotted as a function of the product of the equivalent ideal gas pressure $P_i$ and the inside diameter d of the microballoon. For a 100-$\mu$m-diam glass microballoon filled with 100 atm of DT gas, i.e., $P_i d = 1$ atm.cm, self absorption by the gas decreases the number of x-ray photons generated to about 57 percent of what would be expected in the absence of such absorption.

In Solacells, the tritium beta particles excite the characteristic K$\alpha$ lines of manganese at 5.9 and 7.5 keV, respectively. In contrast, interaction of the beta particles with sodium borosilicate glass microballoons produces a broad bremsstrahlung x-ray peak with a maximum at about 4 keV. In calcium-sodiumborosilicate glass microballoons, the beta particles produce a composite bremsstrahlung/calcium-K$\alpha$ peak with a maximum intensity at about 3.8 keV.

Although these x-rays are quite soft, the thin walls of the microballoons which are 0.5 to 20 $\mu$m thick allow useful transmission of these x-ray photons despite their very low energies. A glass microballoon with a 2-μm-thick wall transmits about 80 percent of the x-ray photons. The metal Solacells—although much more opaque—transmit about 30 percent of the x-ray photons through a 10-μm-thick wall and about 50 percent through a 5-μm-thick wall.

This method measures only the tritium content of the targets directly. However, by filling the microballoons to equilibrium with a supply gas having a known D-T ratio, the D-T ratio in the as-filled targets is also known. Known data for the isotope effect on "hydrogen" permeation through metal and glass walls then permits the deuterium permeation through the walls to be calculated once the tritium loss is determined.

Because of the difficulty of calculating both the production and transmission rates of the x-rays in the various materials involved, it is necessary to produce calibration curves for each type of microballoon which show the variation in x-ray output with tritium content. These calibration curves are produced by measurements made using microballoons of the same materials and with the same range of diameters and wall thicknesses and filled to a variety of pressures.

Thus, when the microballoon material, diameter, and wall thickness are known, the tritium content is readily determined by counting the x-rays produced for a fixed time and comparing the count to the calibration curve for that particular type of microballoon. Once the tritium content is determined, the deuterium content may be readily calculated. It will be readily apparent that this method is applicable with any type of microballoon of a material and having a wall thickness which permits a measurable amount of x-rays to be transmitted from the microballoon.

Counting System

Figure 3:
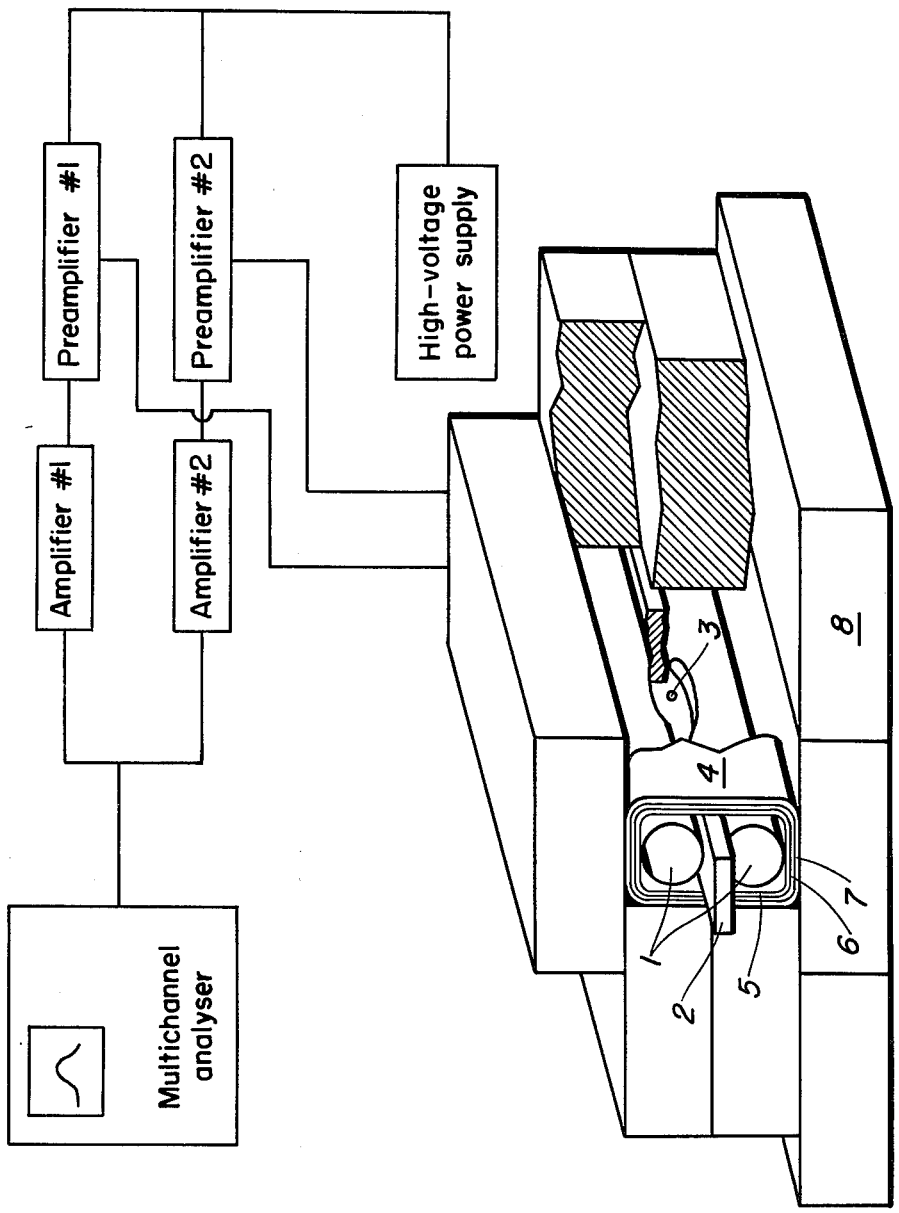
FIG. 3 is a schematic of an x-ray counting system useful with the method of the invention.

A schematic of an x-ray counting system useful in practicing the method of this invention is shown in FIG. 3. Two 5-cm-diam gas-proportional x-ray tubes 1 filled with 1 atm of xenon gas ($CO_2$ quench) and having 2.5-cm-diam windows (not shown) of 50-μm-thick Mylar are arranged with the windows about 0.8 cm apart. A target support tray 2 containing the target 3 to be assayed is inserted into the gap between counters 1. Target 3 is supported near the center of a ~ 100-nm-thick plastic film stretched across a 4-mm-diam hole (not shown) in target support tray 2. Tray 2 is inserted between counters 1 to a point where target 3 is centered between the windows in the counter. This arrangement gives a geometrical counting efficiency of 70 percent. Tubes 1 are surrounded longitudinally by a graded-Z shield 4 consisting of aluminum 5, copper 6, and cadmium 7 foils having thicknesses of 225 μm, 125 μm, and 0.15 cm, respectively. This entire assembly is shielded in ~ 5 cm of lead using bricks 8. With this arrangement, a background count rate of ~ 25 cps is observed.

The counter-tube outputs are ampliifed, mixed, and fed to a multichannel pulse-height analyzer. The amplifiers are balanced using a $^{55}Fe$ x-ray source. The gas-proportional tubes 1 are > 90 percent efficient for all photons with energies up to 11 keV that can penetrate their windows. The window transmission, at normal incidence, of silicon K photons at 1.74 keV is ~ 5 percent so that the contribution of these photons to the observed peak is small. At 4 keV, the corresponding transmission is ~ 75 percent, whereas at 6 and 8 keV, transmission increases to 92 and 98 percent, respectively.

Figure 4:
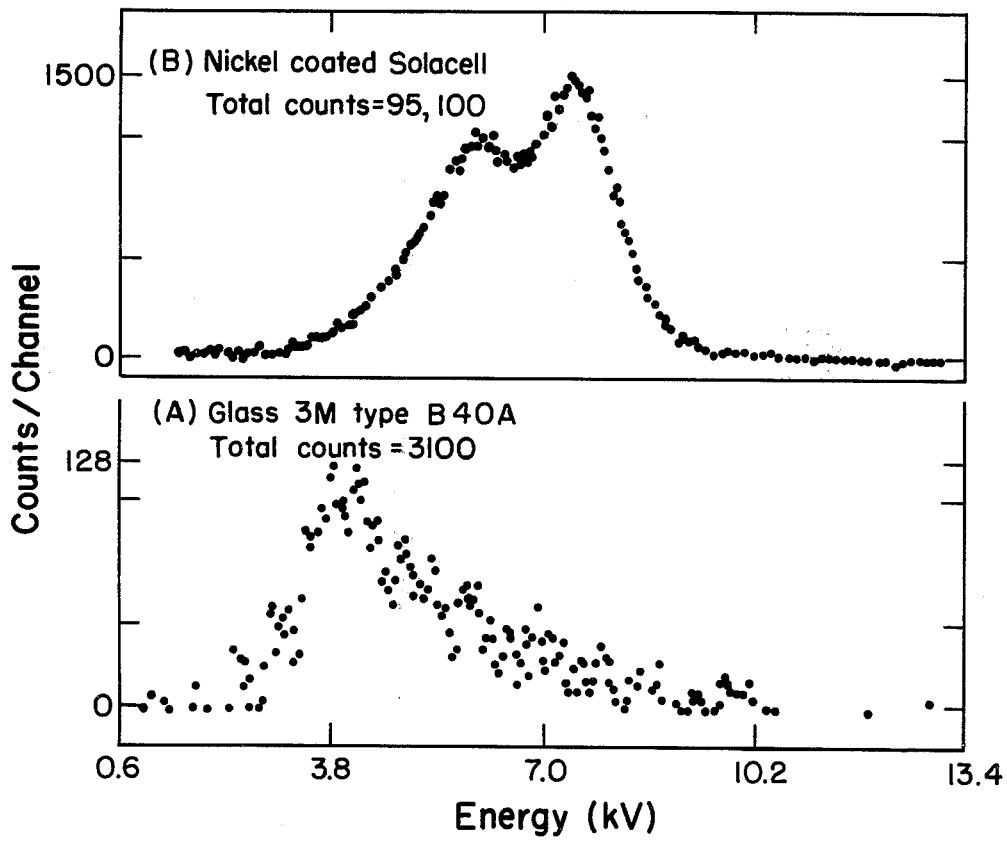
FIG. 4 shows x-ray counter multichannel analyzer outputs for (A) 3M Type B40A glass microballoon, 63-$\mu$m-diam by 1.5-$\mu$m-thick wall, containing 0.8 ng of tritium, and (B) nickel-coated Solacell, 176-$\mu$m-diam by 5.7-$\mu$m-thick wall, containing 83 ng of tritium.

The resolution of the gas-proportional tubes is indicated in FIG. 4 which presents the multichannel analyzer output for a sodium-calcium-borosilicate glass microballoon and for a nickel-plated Solacell, filled with 0.8 and 83 ng of tritium, respectively. The manganese and nickel K $\alpha$ peaks obtained from Solacells can just be resolved, but the calcium K $\alpha$ peak cannot be separated from the bremsstrahlung peak (3.7 and 4 keV, respectively) in glass microballoons. Even so, this resolution is more than adequate for the method of the invention.

Calibration

Calibration data are prpesented in Tables I and II for the glass and metal microballoons, respectively. The glass microballoons are made of calcium-sodium-borosilicate glass, while the metal microballoons consist of a Solacell mandrel with a ~ 1.5-μm-thick wall overcoated with electroless nickel to make up the indicated wall thickness. Fill pressures are measured in accordance with the ideal gas pressure at 298 K equivalent to actual gas density. The gas contents of the individual microballoons are determined by several methods. In one, 16 MeV protons produced in a Van de Graaff generator impinge on the microballoons and recoil deuterons and tritons produced by the elastic scattering reacitons D(p,d)H and T(p,t)H are measured. In another, the gas content is calculated from the known fill conditions, i.e., gas density and composition and size of microballoon. In some instances shown under the heading "Other", destructive assay of the microballoon fuel content was made. The microballoon was either broken in the inlet of a quadrapole mass spectrometer and the composition and amount of the contained gases analyzed by the spectrometer, or the microballoons were broken in an evacuated, known small volume and the resultant pressure rise measured to obtain the total number of moles of gas.

Table I

| Microballoon Size [o.d. × wall (μm)] and Fill Pressure, $P_i$ (atm) | $P_i d$ (atm-cm) | Gas Content (ng) | | | X rays (counts/s) | X-ray Calibration (counts/s-ng) | |
|---|---|---|---|---|---|---|---|
| | | Calculated | Van de Graaff | Other | | Measured | Corrected |
| 98 × 1.8 | 0.524 | 5.9 T | 5.8 ± 0.6 T | — | 30.6 | 5.2 | 7.3 |
| 55.5 | | 0.1 D | 0.2 ± 0.2 D | — | | | |
| 100.4 × 1.4 | 0.807 | 5.8 T | 4.7 ± 0.6 T | — | 21.6 | 3.7, 4.6 | 6.0, 7.4 |
| 82.7 | | 2.8 D | 2.7 ± 0.4 D | — | | | |
| 111.9 × 1.4 | 0.902 | 8.1 T | 8.7 ± 0.9 T | 7.6 T | 33.1 | 4.1, 3.8, 4.4 | 6.9, 6.4, 7.4 |
| 82.7 | | 3.9 D | 4.5 ± 0.5 D | 3.9 D | | | |
| 78.9 × 2.1 | 0.618 | 2.6 T | 2.6 ± 0.6 T | — | 10.5 | 4.0 | 5.9 |
| 82.7 | | 1.2 D | 0.9 ± 0.4 D | — | | | |
| 75.5 × 2.1 | 0.590 | 2.2 T | 2.0 ± 0.5 T | — | 9.5 | 4.3, 4.8 | 6.2, 7.0 |
| 82.7 | | 1.1 D | 1.3 ± 0.3 D | — | | | |

Table I-continued

| Microballoon Size [o.d. × wall (μm)] and Fill Pressure, $P_i$ (atm) | $P_i d$ (atm-cm) | Gas Content (ng) | | | X rays (counts/s) | X-ray Calibration (counts/s-ng) | |
|---|---|---|---|---|---|---|---|
| | | Calculated | Van de Graaff | Other | | Measured | Corrected |
| | | | | | | Average: 6.7 ± 0.6 (1σ) | |

Table II

| Microballoon Size [o.d. × wall (μm)] and Fill Pressure, $P_i$ (atm) | $P_i d$ (cm-atm) | Gas Contents (ng) | | | Calculated Wall Transmission (%) | X ray (counts/s) | X-ray Calibration (counts/s-ng) | | |
|---|---|---|---|---|---|---|---|---|---|
| | | Calculated | Van de Graaff | Other | | | As-measured | Corrected | Normalized |
| 150.4 × 5.4 344 | 4.8 | 68.3 T 35.1 D | 58.8 ± 3 T 35.3 ± 2 D | | 44 | 90.9 | 1.43 | 8.36 | 19.0 |
| 154.7 × 5.4 344 | 4.9 | 74.8 T 38.5 D | 75.2 ± 3 T 38.5 ± 2 D | 67.2 T 34.7 D | 44 | 78.3 | 1.08 | 6.45 | 14.7 |
| 175 × 7.0 320 | 5.1 | 80.2 T 60.7 D | 83.1 ± 3 T 61.3 ± 3 D | | 36 | 104.5 | 1.28 | 7.80 | 21.7 |
| 178 × 7.0 320 | 5.2 | 84.8 T 64.2 D | 92.2 ± 3 T 64.1 ± 3 D | | 36 | 108.7 | 1.23 | 7.59 | 21.1 |
| 145.8 × 8.1 344 | 4.5 | 54.7 T 28.1 D | 54.4 ± 2 T 28.1 ± 2 D | | 33 | 89.6 | 1.64 | 9.65 | 29.2 |
| 170.6 × 9.7 344 | 5.2 | 86.8 T 44.6 D | 82.3 ± 4 T 41.5 ± 2 D | a. | 28 | 77.1 | 0.91 | 5.62 | 20.1 |
| — | — | | 42.9 ± 3 T 24.6 ± 2 D | b. | | 73.7 | 1.72 | — | |
| | | | | | | Average (without 8.1 μm wall): 19.3 ± 2.8 (1σ) | | | | a. 1.8 × 10⁻⁸ mole by ΔP method. Values of 2.4 × 10⁻⁸ mole and 2.2 × 10⁻⁸ mole are obtained from the calculated and Van de Graaff measured contents, respectively.

b. 1.3 × 10⁻⁸ mole by ΔP method. A value of 1.3 × 10⁻⁸ mole is obtained from the Van de Graaff measured contents.

Figure 5:
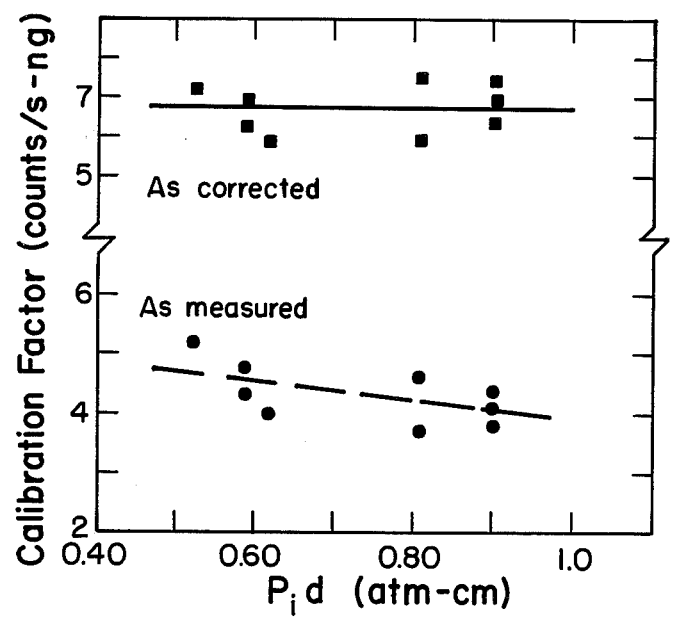
FIG. 5 shows x-ray calibration factors for glass microballoons illustrating the effect of the self-absorption corrections.

The glass microballoon data are corrected for self absorption, according to FIG. 2, to obtain the values listed in the last column of Table I. As expected, the effect of glass wall thickness on the calibration factor is smaller than the data scatter, so all data are averaged to obtain 6.7 ± 0.6 counts/s-ng, under negligible self-absorption conditions. The effect of the self-absorption correction is illustrated in FIG. 5 where the as-measured and as-corrected calibration factors are plotted versus $P_i d$. The as-measured data clearly decrease with increasing $P_i d$, while any dependence of the as-corrected values is masked by the data scatter.

The metal microballoon data in Table II are complicated both by self absorption of the tritium beta particles and by appreciable x-ray absorption in the metal walls. The former is corrected for using the data in FIG. 2 to obtain the corrected calibration factors listed in column 9 of the table. Then, approximate x-ray transmission of the metal walls is calculated from mass absorption coefficients at 5.9 and 7.4 keV, weighted according to the relative peak heights observed at these two energies. A 1.5-μm-thick inner shell of 76 Ni:24 Mn alloy (i.e., the Solacell) is assumed, surrounded by a second shell of pure nickel to make up the balance of the wall thickness. The corrected calibration factors (column 9) are then normalized to zero wall thickness and are listed in column 10. Ignoring the data for the apparently anomalous 8.1-μm-thick wall, the average of these normalized data is 19.3 ± 2.8 counts/s-ng.

The sensitivity of the x-ray assay method of the invention is rather high. As stated earlier, the background count rate in the counting system is ∼ 25 cps. Therefore, with a counting time of 1000 s, 0.5 ng of tritium in a glass microballoon can be assayed to a statistical counting uncertainty of ± 7.7 percent. The larger metal microballoons, similar to those in Table II, usually contain a minimum of ∼ 8 ng of tritium, in which case counting statistics errors are less than ± 1.5 percent for counting times of 1000 s.

Application

This assay method is very useful in estimating gas-retention half-lives of individual targets. In this case, a series of measurements is made on a particular microballoon as a function of time. After correcting these data for the pressure-dependent tritium beta self absorption, the time required for one-half of the initial gas content to be lost is calculated. Because both the material and wall thickness of any individual microballoon are constant with time, no other calibration is required. Additionally, by comparing a series of microballoons of the same type having similar sizes and initial pressures, relative half-lives can be obtained even without applying the self-absorption correction. The measurement of gas-retention half-lives of microballoons is of major concern in learning how to fabricate laser fusion targets.

Figure 6:
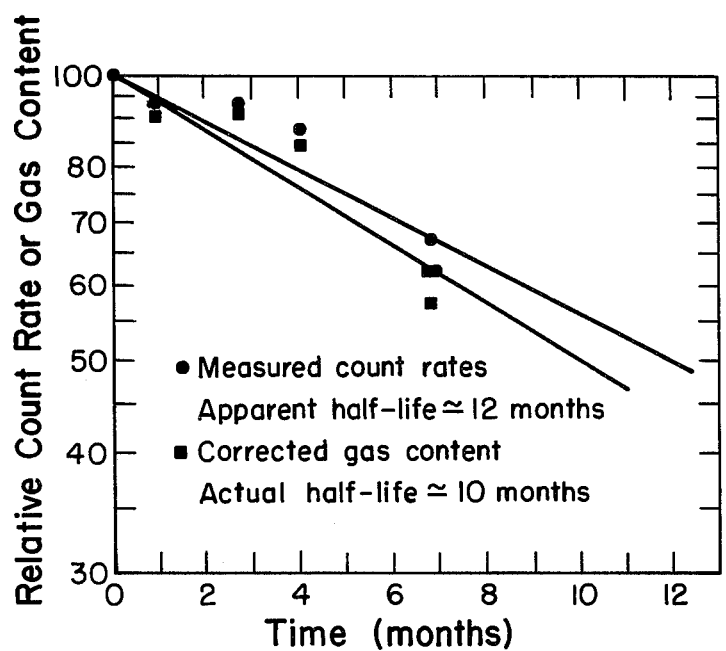
FIG. 6 shows tritium gas-retention half-life measurement data for a low-permeability glass microballoon.

A typical set of data is presented in FIG. 6 for a sodium-calcium-borosilicate glass microballoon (Type B40A from Minnesota Mining & Mfg. Co.). This microballoon was 53-μm outside diameter with a wall of 1.5 μm. It was filled to an equivalent ideal gas pressure (298 K) of 60 atm, so the initial $P_i d$ factor is 0.30 atm.cm. In this case the count rate data indicate an apparent half-life of about 12 months; when tritium beta self absorption is corrected for via the data in FIG. 2, the actual half-life is about 10 months. The error in half-lives estimated directly from the count rate data increases with increasing values of $P_i d$; if data are obtained over one half-life for glass microballoons with initial $P_i d$ values of 2, 1, and 0.5 atm.cm, the indicated half-lives will be ∼ 2, 1.6, and 1.3 times longer than the actual values. The relative errors are somewhat larger for metal microballoons.

Figure 7:
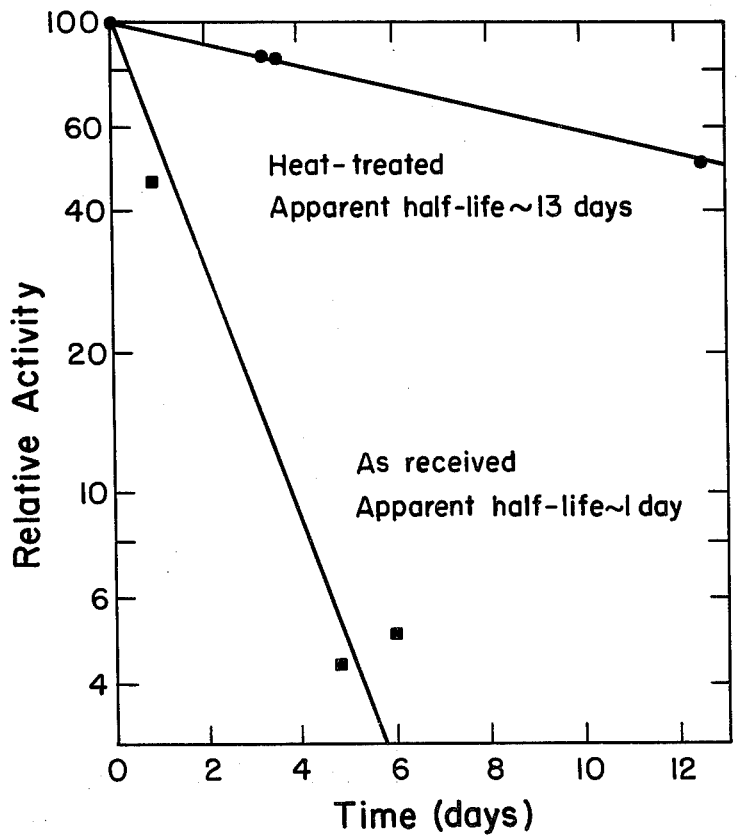
FIG. 7 shows relative tritium gas-retention half-life measurements for high-permeability glass microballoons.

A comparative half-life measurement is illustrated in FIG. 7 for low-sodium borosilicate glass microballoons (SI-Eccospheres obtained from Emerson and Cuming Company, Canton, Mass.). The lower curve is for an as-received microballoon with an apparent half-life of ~ 1 day. Heat treatment for 20 h at 975 K in flowing hydrogen sinters the structure of these microballoons and decreases the permeability so that their apparent half-life increases to ~ 13 days (upper curve). These apparent half-lives are too long by a factor of ~ 1.2, but the error in the relative value should be substantially less than this.

In addition to this half-life application, it is advantageous to routinely assay the tritium content of all laser fusion targets before mounting them in the target chamber for laser/target interaction experiments. In this case, calibration data are utilized to determine the tritium content directly. In addition, it is desirable to assay every tritium-filled microballoon immediately after filling with gas. Since the microballoons are typically filled to equilibrium with the supply gas, the gas density and the composition in the as-filled microballoon is therefore known. Counting the x-rays from these as-filled microballoons gives a direct calibration of the counting system for each individual microballoon, which can then be used to calculate the tritium content at some later time if the fractional decrease in x-ray count rate is measured and the appropriate tritium beta self-absorption correction is applied.

What we claim is:

1. A method of nondestructively determining the deuterium and tritium contents of laser fusion target microballoons which comprises (a) counting the x rays produced by the interaction of tritium beta particles with the walls of said microballoons, (b) comparing the number of counts for a designated period of time with a calibration curve of counts for various tritium contents for the same designated time period to obtain the tritium content, and (c) calculating the deuterium content utilizing the known initial D-T ratio and the known diffusion rates for D and T.

2. The method of claim 1 wherein said microballoons have a wall thickness in the range of 0.5 to 20 $\mu$m.

3. The method of claim 2 wherein said microballoons are metal microballoons.

4. The method of claim 2 wherein said microballoons are glass microballoons.

* * * * *